(12) United States Patent
Houen et al.

(10) Patent No.: US 9,140,691 B2
(45) Date of Patent: Sep. 22, 2015

(54) DIAGNOSTIC BLOOD TEST USING ADSORPTION ON FILTER PAPER

(75) Inventors: Gunnar Houen, Virum (DK); David Hougaard, Virum (DK); Kristin Skogstrand, Copenhagen S (DK); Charlotte Svaerke Jørgensen, Holmegaard (DK)

(73) Assignee: Statens Serum Institut, Copenhagen (DK)

( * ) Notice: Subject to any disclaimer, the term of this patent is extended or adjusted under 35 U.S.C. 154(b) by 1348 days.

(21) Appl. No.: 11/948,264

(22) Filed: Nov. 30, 2007

(65) Prior Publication Data

US 2008/0153116 A1 Jun. 26, 2008

Related U.S. Application Data

(60) Provisional application No. 60/873,789, filed on Dec. 8, 2006.

(30) Foreign Application Priority Data

Dec. 1, 2006 (DK) ................................ 2006 01587

(51) Int. Cl.
| | | |
|---|---|---|
| G01N 33/52 | (2006.01) | |
| G01N 33/48 | (2006.01) | |
| G01N 33/92 | (2006.01) | |
| G01N 33/66 | (2006.01) | |
| G01N 33/68 | (2006.01) | |

(52) U.S. Cl.
CPC .............. *G01N 33/521* (2013.01); *G01N 33/48* (2013.01); *G01N 33/66* (2013.01); *G01N 33/68* (2013.01); *G01N 33/92* (2013.01); *Y10T 436/143333* (2015.01)

(58) Field of Classification Search
CPC ....... G01N 33/48; G01N 33/66; G01N 33/68; G01N 33/92
See application file for complete search history.

(56) References Cited

U.S. PATENT DOCUMENTS 6,331,541 B1 * 12/2001 Ko et al. ..................... 514/237.2
2004/0121305 A1 6/2004 Wiegand et al.

FOREIGN PATENT DOCUMENTS

JP 10201500 8/1998

OTHER PUBLICATIONS

Campiglia et al., (Analytica Chimica Acta. 1998. vol. 372:349-355).*
Jafri et al., (Am. J. Trop. Med. Hyg. 1998. vol. 58(3):313-315).*
Stickle et al., (Am. J. Clinical Pathol. 2003. vol. 119:292-297).*
Andersen, et al., "Cytotoxic T cells", J. Invest. Dermatol., 126(1):32-41 (Jan. 2006).
Anderson, et al., "The human plasma proteome: history, character, and diagnostic prospects", Mol. Cell Proteomics, 1(11): 845-867 (Nov. 2002).
Blach-Olszewska, Z., "Innate immunity: cells, receptors, and signaling pathways", Arch. Immunol. Ther. Exp., 53(3):245-253 (May-Jun. 2005).
Bousso, P., "Generation of MHC-peptide tetramers: a new opportunity for dissecting T-cell immune responses", Microbes Infect., 2(4):425-429 (Apr. 2000).
Cravens, et al., "Dendritic cells, chemokine receptors and autoimmune inflammatory diseases", Immunol. Cell Biol., 80(5):497-505 (Oct. 2002).
Hogrefe, WR., "Biomarkers and assessment of vaccine responses", Biomarkers, 10 (Suppl 1):S50-S57 (Nov. 2005).
House, RV., "Theory and practice of cytokine assessment in immunotoxicology", Methods, 19(1):17-27 (Sep. 1999).
Jerome, et al., "Measurement of CTL-induced cytotoxicity: the caspase 3 assay", Apoptosis, 8(6):563-71 (Dec. 2003).
Kano, et al., "Direct detection of dermatophytes in skin samples based on sequences of the chitin synthase 1 (CHS1) gene", J. Vet. Med. Sci., 65(2):267-270 (Feb. 2003).
Lapidot, et al., "Current understanding of stem cell mobilization: the roles of chemokines, proteolytic enzymes, adhesion molecules, cytokines, and stromal cells", Exp. Hematol., 30(9):973-981 (Sep. 2002).
Manz, et al., "Maintenance of serum antibody levels", Annu. Rev. Immunol., 23:367-86 (Apr. 2005 ; e-pub Nov. 19, 2004).
Mei, et al., "Use of filter paper for the collection and analysis of human whole blood specimens", J. Nutr., 131(5):1631S-1636S (May 2001).
Meidenbauer, et al., "Direct visualization of antigen-specific T cells using peptide-MHC-class I tetrameric complexes", Methods, 31(2):160-171 (Oct. 2003).
Norgaard-Pedersen, et al., "Biological specimen banks in neonatal screening", Acta. Paediatr. Suppl., 88(432):106-109 (Dec. 1999).
Schmittel, et al., "Quantification of tumor-specific T lymphocytes with the ELISPOT assay", J. Immunother., 23(3):289-295 (May-Jun. 2000).
Skogstrand, et al., "Simultaneous measurement of 25 inflammatory markers and neurotrophins in neonatal dried blood spots by immunoassay with xMAP technology", Clin. Chem., 51(10):1854-1866 (Oct. 2005 ; e-pub Aug. 4, 2005).

(Continued)

*Primary Examiner* — Rodney P Swartz
(74) *Attorney, Agent, or Firm* — Howson & Howson LLP

(57) ABSTRACT

A diagnostic test and method is provided comprising mixing blood or another biological fluid sample with a test compound and spotting the blood on filter paper for subsequent analysis of the effect of the test compound on the blood. The biological fluid can be a cerebrospinal fluid, a peritoneal fluid, a cyst fluid, an amniotic fluid, a lavage fluid, a saliva, a cell extract or a tissue extract. The compound is chosen among an amino acid, a peptide, a protein, a carbohydrate, an oligosaccharide, a polysaccharide, a glycoprotein, a lipid, a lipoprotein, a glycosaminoglycan, a hormone, a steroid, a vitamin, a low molecular weight synthetic or natural compound which influences the blood to cause an alteration of its composition, e.g., a toxin, allergen, autoantigen, bacterial protein or polysaccharide, viral protein, fungal protein or polysaccharide, parasitic protein or polysaccharide, bacterial lipopolysaccharide or any other compound relevant to diseases.

7 Claims, No Drawings

(56) References Cited

OTHER PUBLICATIONS

Steinke, et al., "Cytokines and chemokines", J. Allergy Clin. Immunol., 117(2 Suppl Mini-Primer):S441-S445 (Feb. 2006).
Stelzer, et al., "Flow cytometric evaluation of leukocyte function", Diagn. Clin. Immunol., 5(5):223-31 (1988).
Thadikkaran, et al., "Recent advances in blood-related proteomics", Prteomics, 5(12):3019-3034 (Aug. 2005).
Troutt, et al., Quantitative analysis of lymphokine expression in vivo and in vitro, Immunol. Cell Biol., 70 ( Pt 1):51-57 (Feb. 1992).
Villas, BH., "Flow cytometry: an overview", Cell Vis., 5(1):56-61 (Jan.-Feb. 1998).
Aburuz, et al: "Dried blood spot liquid chromatography assay for therapeutic drug monitoring of metformin" Journal of Chromatography B: Biomedical Sciences & Applications, Elsevier, Amsterdam, NL, vol. 832, No. 2, available online Jan. 30, 2006, pp. 202-207.
Beaudette, et al: "Discovery stage pharmacokinetics using dried blood spots" Journal of Chromatography B: Biomedical Sciences & Applications, Elsevier, Amsterdam, NL, vol. 809, No. 1, available online Jul. 4, 2004, pp. 153-158.
Gelb, et al: "Direct multiplex assay of enzymes in dried blood spots by tandem mass spectrometry for the newborn screening of lysosomal storage disorders" Journal of Inherited Metabolic Disease, Kluwer Academic Publishers, DO, vol. 29, No. 2-3, Apr. 1, 2006, pp. 397-404, footer: "presented at the 42nd Annual Meeting of the SSIEM, Paris, Sep. 6-9, 2005".
Koal, et al: "Quantification of antiretroviral drugs in dried blood spot samples by means of liquid chromatography/tandem mass spectrometry" Rapid Communications in Mass Spectrometry : RCM 2005, vol. 19, No. 21, online Sep. 29, 2005, pp. 2995-3001.
Parker, et al: "Use of dried blood spots for the detection and confirmation of HTLV-I specific antibodies for epidemiological purposes." Journal of Clinical Pathology, vol. 48, No. 10, Oct. 1995, pp. 904-907.
Skogstrand, et al.: "Antigen-induced cytokine and chemokine release test for tuberculosis infection using adsorption of stimulated whole blood on filter paper and multiplex analysis" Scandinavian Journal of Clinical & Laboratory Investigation, vol. 72, pp. 204-211, e-pub Jan. 27, 2012.
Jan. 9, 2009 International Preliminary Report on Patentability in corresponding International Patent Application No. PCT/DK2007/000528 (common priority with the present application).
Oct. 7, 2009 Communication in European Patent Application No. 07817923.1, regional stage of International Patent Application No. PCT/DK2007/000528.
Feb. 17, 2010 Response to Oct. 7, 2009 Communication in European Patent Application No. 07817923.1.
Jun. 2, 2010 Communication in European Patent Application No. 07817923.1.
Sep. 30, 2010 Response to Jun. 2, 2010 Communication in European Patent Application No. 07817923.1.
Jul. 4, 2013 Summons to attend oral proceedings in European Patent Application No. 07817923.1.
Oct. 9, 2013 Response to Summons to attend oral proceedings in European Patent Application No. 07817923.1.
Oct. 16, 2013 Result of Consultation on Oct. 11, 2013 in European Patent Application No. 07817923.1.
Oct. 31, 2013 Response to Result of Consultation in European Patent Application No. 07817923.1.
Nov. 7, 2013 Revised set of claims in European Patent Application No. 07817923.1.
Nov. 27, 2013 Communication of intention to grant in European Patent Application No. 07817923.1.

\* cited by examiner

DIAGNOSTIC BLOOD TEST USING ADSORPTION ON FILTER PAPER

CROSS-REFERENCE TO RELATED APPLICATIONS

This application claims the benefit under 35 USC 119(e) of prior U.S. Provisional Patent Application No. 60/873,789, filed Dec. 8, 2006.

BACKGROUND OF THE INVENTION

Blood is a complex mixture composed of plasma and cells [(Beck W S (Ed.). Hematology. MIT Press 1985; Bloom A L, Thomas, D P (Eds.). Haemostasis and thrombosis. Longman 1987; Janeway C A, et al., Immunobiology. Elsevier 1999)]. The plasma can be separated from the cells by centrifugation and other techniques. If the plasma is allowed to stand it will clot by coagulation and serum may be separated from the blood clot. The coagulation may be inhibited by addition of various anticoagulants, including EDTA, EGTA, heparin, citrate and others. The cells of the blood include dendritic cells, macrophages, monocytes, neutrophils, T lymphocytes, B lymphocytes, natural killer cells, red blood cells and various stem cells including hemopoietic stem cells. In addition megakaryocyte-derived platelets are present in large numbers. The plasma contains thousands of proteins, in principle any protein of the human proteome [Thadikkaran L, et al, Recent advances in blood-related proteomics. *Proteomics.* 2005; 5:3019-34; Anderson N L and Anderson N G. The human plasma proteome: history, character, and diagnostic prospects. *Mol Cell Proteomics.* 2002; 1:845-67)]. Some of the proteins are involved in transport, blood clotting or immune defence, while others function as signalling molecules between cells of the blood and cells of the tissues. In particular, the activity of the cells of the immune system (dendritic cells, macrophages, T cells, B cells, natural killer cells) is regulated by a complex network of signalling molecules (e.g. interleukins, chemokines, growth factors), tissue antigens and receptors (Janeway, cited above; Steinke J W, et al, Cytokines and chemokines. *J Allergy Clin Immunol.* 2006; 117:S441-5; Blach-Olszewska Z. Innate immunity: cells, receptors, and signaling pathways. *Arch Immunol Ther Exp.* 2005; 53:245-53. Lapidot T, Petit I.

Current understanding of stem cell mobilization: the roles of chemokines, proteolytic enzymes, adhesion molecules, cytokines, and stromal cells. *Exp Hematol.* 2002; 30:973-81. Cravens P D, Lipsky P E. Dendritic cells, chemokine receptors and autoimmune inflammatory diseases. *Immunol Cell Biol.* 2002; 80:497-505.] The activity and specificity of immune system cells can be investigated and quantitated by several methods and assays. T cells, B cells and other cells can be quantitated by fluorescence-activated cell sorting using antibodies to cell surface marker molecules (Villas B H. Flow cytometry: an overview. *Cell Vis.* 1998; 5:56-61. Stelzer G T, Robinson J P. Flow cytometric evaluation of leukocyte function. *Diagn Clin Immunol.* 1988; 5:223-31.] Specific T cells can be measured by cytotoxicity assays, chromium release assays and cytokine release assays (e.g. ELISPOT) (Jerome K R, et al., Measurement of CTL-induced cytotoxicity: the caspase 3 assay. *Apoptosis.* 2003; 8:563-7; Andersen M H, et al, Cytotoxic T cells. *J Invest Dermatol.* 2006; 126:32-41. Troutt A B, et al, Quantitative analysis of lymphokine expression in vivo and in vitro. *Immunol Cell Biol.* 1992; 70:51-7; Schmittel A, et al., Quantification of tumor-specific T lymphocytes with the ELISPOT assay. *J Immunother.* 2000; 23:289-95; House R V. Theory and practice of cytokine assessment in immunotoxicology. Methods. 1999; 19:17-27.) and by using various peptide-major histocompatibility complex (MHC) protein constructs (Meidenbauer N, et al, Direct visualization of antigen-specific T cells using peptide-MHC-class I tetrameric complexes. Methods. 2003; 31:160-71; Bousso P. Generation of MHC-peptide tetramers: a new opportunity for dissecting T-cell immune responses. *Microbes Infect.* 2000; 2:425-9). The activity of B cells can be measured by determining the levels of specific antibodies released from the B cells (Hogrefe W R. Biomarkers and assessment of vaccine responses. Biomarkers. 2005; 10:S50-7; Manz R A, et al, Maintenance of serum antibody levels. *Annu Rev Immunol.* 2005; 23:367-86).

A major problem in measuring signalling molecules released from blood cells is that of storage and transport in relation to quantitation. Many blood constituents (e.g. cytokines) are labile and short lived, resulting in degradation during incubation, storage and transport. For this reason, comparative analyses and diagnostic tests have to be carried out immediately upon blood collection and incubation in central laboratories. Ideally, all samples to be compared should be analyzed consecutively using a calibrated instrument.

This is not always practical, e.g. when taking blood samples in remote areas, when doing in vitro and in vivo time-studies or when comparing samples from many different individuals. One solution to this problem is to freeze samples for transport and storage. This, however, does not guarantee preservation of constituents, requires large freezing, transport and storage capacity, requires thawing each time an analysis is performed, and is vulnerable with regard to shortage of electric power supply. For this reason, there is a need for reliable methods of blood and biological sample preservation and a need for diagnostic tests employing reliable sample preservation in combination with sample manipulation.

The use of filter paper for spotting blood for subsequent analysis is well known, e.g. for analysis of blood samples of newborn babies for inherited metabolic diseases (Mei J V, et al., Use of filter paper for the collection and analysis of human whole blood specimens. *J Nutr.* 2001; 131:1631S-6S. The advantages of this are good preservation of blood constituents, easy transport and facile long term storage. However, the use of filter paper and similar methods for drying and storing blood samples after incubation with test compounds has not been used or described before, possibly because this has been anticipated to be impossible or impractical.

What are needed are improved methods for transporting and storing biological samples.

SUMMARY OF THE INVENTION

A diagnostic test and method is provided for mixing blood or another biological fluid or sample with a test compound and spotting the blood on filter paper for subsequent analysis of the effect of the test compound on the blood or fluid sample.

In another aspect, the invention permits spotting the blood on filter paper for drying, preservation and subsequent analysis of the effect of the test compound on the blood.

Other aspects and advantages of the invention will be apparent from the following detailed description of the invention.

DETAILED DESCRIPTION OF THE INVENTION

A diagnostic test and method are provided comprising mixing blood or another biological fluid sample with a test compound and spotting the blood on filter paper for subsequent analysis of the effect of the test compound on the blood.

As used herein, the biological fluid can be readily selected from any suitable biological fluid including, e.g., a cerebrospinal fluid, a peritoneal fluid, a cyst fluid, an amniotic fluid, a lavage fluid, a saliva, urine, vaginal fluids, semen, tears, a cell extract or a tissue extract.

As used herein, a "test compound" can be selected from any suitable source. Examples of suitable test compounds include, without limitation, an amino acid, a peptide, a protein, a carbohydrate, an oligosaccharide, a polysaccharide, a glycoprotein, a lipid, a lipoprotein, a glycosaminoglycan, a hormone, a steroid, a vitamin, a natural or synthetic chemical compound which influences the blood to cause an alteration of its composition, e.g., a toxin, allergen, autoantigen, bacterial protein or polysaccharide, viral protein, fungal protein or polysaccharide, parasitic protein or polysaccharide, bacterial lipopolysaccharide, a nucleic acid sequence (including a DNA or an RNA), or any other compound relevant to diseases.

The diagnostic test and method according to the invention analyses the sample for the content of cytokines, chemokines and growth factors and/or neurotransmitters and other polypeptides and proteins, e.g., C-reactive protein (CRP), immunoglobulin (Ig) IgG, IgA, IgM, IgD, IgE, specific (i.e., antigen specific) antibodies, transferrin, albumin and/or transthyretin (TTR).

In the diagnostic test the effect of the test compound is analyzed by immunoassay, bioassay, mass spectrometry, high performance liquid chromatography (HPLC), gas chromatography (GC), GC-MS, e.g., enzyme-linked immunosorbent assays (ELISA), fluorophore-linked immunosorbent assays (FLISA), dissociation-enhanced lanthanide fluoroimmunoassay (DELFIA), x-mapping assays, (e.g., LUMINEX® (x-mapping) assays), luminescence assays, electrochemiluminescence assays, scintillation proximity assays, radioimmunoassays, matrix assisted laser desorption/ionization (MALDI)-MS, electrospray ionization (ESI)-MS and ambient-MS (e.g., desorption ESI, DESI-MS), polymerase chain reaction (PCR), and reverse transcript (RT)-PCR.

This invention also discloses a method of mixing blood or another biological fluid or sample with a test compound and spotting the mixture on filter paper for storage, transport and/or handling before subsequent analysis of the effect of the test compound on the blood, biological fluid or sample.

DEFINITIONS

Analyte means any compound which can be detected or quantitated by analytic means.

By the effect of test compound is understood that it interacts with constituents of the blood or any other biological fluid or sample to cause an alteration in the composition of the blood of any kind.

Drying means removal of water.

Filter paper means any piece of paper, cloth or other material suitable for collecting, drying and storing blood. Examples of suitable filter paper are available commercially include, e.g., Whatman filter paper [Whatman, Brentford, Middlesex, UK]. Filter paper typically has a thickness in the range of 0.5 mm-1.2 mm. For example, blood collection filter paper cards are available from Schleicher and Schuell (Keene, N H, recently acquired by Whatman). Suitably, the paper selected is manufactured according to the specifications set by the US national committee for clinical laboratory standards for blood collection. Other sizes of filter paper, and other brands can be readily selected.

PKU paper means paper/filter paper used for screening of blood samples from newborn babies for phenyl ketonuria (PKU) syndrome. Examples of suitable PKU paper includes that available commercially, e.g., from Whatman Schelicer & Schuell 2992 or 903.

Spotting means the application of a blood sample or any other biological fluid or extract or sample to a piece of standardised paper suitable for accurate blood sampling. The spotting is done by applying a fixed volume of blood to a piece of paper or by applying blood to the paper until a defined area is covered with blood. Subsequently, the paper is allowed to dry completely and either stored immediately at low humidity conditions or transported to a storage place for subsequent analysis.

Test compound means any chemical, biological or physical compound or substance which can be mixed with or added to blood or any other biological fluid or sample.

Test sample means any formulation or mixture of test compounds.

The following abbreviations are used:
BCG means *Bacillus* Calmette-Guerin.
BDNF means brain-derived neurotrophic factor.
BSA means bovine serum albumin.
CRP means C-reactive protein.
DBSS means dried blood spot sample.
DELFIA means dissociation-enhanced lanthanide fluoroimmunoassay.
DESI-MS means Desorption Electrospray Ionization (DESI) Mass Spectrometry.
EGF means epidermal growth factor.
ELISA means enzyme-linked immunosorbent assay.
ELISPOT means enzyme-linked immunospot assay.
ESI means electrospray ionization.
FLISA means fluorescence-linked immunosorbent assay.
GC means gas chromatography.
GC-MS means gas chromatography mass spectrometry.
G-CSF means granulocyte-colony-stimulating factor.
GM-CSF means granulocyte-macrophage colony stimulating factor.
HPLC means high performance liquid chromatography.
IFN means interferon.
Ig means immunoglobulin.
IGF means insulin-like growth factor.
Il means interleukin.
LPS means lipopolysaccharide.
MALDI means matrix-assisted laser desorption/ionization.
MALDI-MS means matrix-assisted laser desorption/ionization mass spectrometry.
M-CSF means macrophage-colony-stimulating factor.
MCP means monocyte chemoattractant protein.
MHC means major histocompatibility complex.
MIF means macrophage migration inhibitory factor.
MIP means macrophage inflammatory/inhibitory protein.
MMP means matrix metallo protease.
MS means mass spectrometry.
NT means neurotrophin.
PBS means phosphate-buffered saline.
PCR means polymerase chain reaction.
PKU means phenyl ketoneuria.
PPD means purified protein derivative.
TGF means transforming growth factor.
TNF means tumor necrosis factor.
TREM means triggering receptor expressed on myeloid cells.
VEGF means vascular endothelial growth factor.

A diagnostic method is provided where the reaction between a test compound and a blood sample or any other biological fluid or sample is initiated, allowed to proceed for a certain time and then stopped by spotting and/or drying the test sample on a filter paper which is then used subsequent for analysis of the effect of the test compound on the blood, fluid or sample and any of their constituents.

In one embodiment, a blood sample (e.g., 10 ml) is drawn from a person using standard anti-coagulation EDTA, heparin or citrate blood containers or glasses. The blood sample is divided in two aliquots and a test compound is added to one aliquot of blood, while the other aliquot is used as a control reference to which only the buffer/solution in which the test compound is dissolved is added. The test compound may also be added as a solid powder to be dissolved directly in the blood. The blood samples are incubated at ambient room temperature or a defined temperature (e.g., 5° C., 20° C., 37° C.) with or without mixing or agitation. At certain time intervals (e.g. 0, 1 min, 2 min, 5 min, 10 min, 20 min, 30 min, 1 h, 2 h, 3 h, 4 h, 5 h, 10 h, 15 h, 20 h, 24 h, 48 h), aliquots are drawn from the blood samples and spotted on filter paper (e.g., PKU paper) and allowed to dry as rapid as possible. After drying, the filter paper may be used immediately for analysis or stored for subsequent analysis. In one embodiment, the filter paper is transported (e.g., by ordinary mail) over a distance before storage or analysis in a laboratory.

Spotting, drying and storage of blood are carried out as follows. Blood is spotted on filter paper with a capillary tube, pipette or similar in one layer and dried at room temperature, e.g., in a well ventilated hood or in an ambient place. For storage, the filter papers may be kept in paper envelopes, plastic bags or similar containers, preferably air tight containers to keep the humidity as low as possible. A storage temperature of −20° C. or lower is preferable, but room temperature is also possible as long as the paper is kept dry. However, the storage may take place at ambient temperature or at a temperature below 0° C. (e.g., −20° C., −50° C., −80° C., −180° C.) provided that the humidity is kept low to avoid deterioration of the samples. Samples can be stored for extended periods of time (e.g., months—years).

The test compounds may be any compound which influences blood to cause a measurable alteration of its composition. Particularly useful test compounds are toxins, allergens, autoantigens, bacterial proteins and polysaccharides, viral proteins, fungal proteins and polysaccharides, parasitic proteins and polysaccharides, bacterial lipopolysaccharides, and any other compound relevant to diseases. Use of these test compounds will lead to important knowledge about how a certain compound affects the cells and the signalling between the cells.

In one embodiment, the diagnostic test and method is used for determining the effect of toxic compounds on blood, e.g., as part of a toxicological test program or a preclinical test program.

Analysis of the dried blood samples may be carried out by a number of different techniques, including the types of assays described above. Particularly desirable methods of analysis are ELISA assays, FLISA assays, DELFIA assays, LUMINEX® assays, luminescence assays, electrochemiluminescence assays, scintillation proximity assays, radioimmunoassays, MALDI-MS, ESI-MS, and PCR.

Extraction of DBSS may be carried out by the use of any suitable buffer or solvent. In one embodiment, filter paper disks, e.g., 3.2 mm in diameter, are punched out from DBSS or standards on filter paper and placed together in microtiter wells. 140 µl or 180 µl (for double- or triple-measurements, respectively) extraction buffer, PBS containing "Complete protease inhibitor cocktail with ethylenediamine tetra-acetic acid (EDTA)" (Roche, Germany) 1 tablet dissolved per 25 ml assay buffer (PBS containing 0.5% Tween 20 and 1% BSA), are added to each well and the analytes are extracted protected from light at room temperature on a plate shaker set at 600 rpm for 60 minutes.

In one embodiment of the invention, analytes are measured by a LUMINEX® assay as follows. Coupling of capture antibodies to carboxylated beads (Luminex corp., Austin Tex., US) is performed according to the manufacturer's instruction: $2.5 \times 10^6$ beads are washed twice with activation buffer (0.1 mol/l sodium phosphate, pH 6.2), re-suspended in 80 µl activation buffer and sonicated until a homogenous distribution of the beads are observed. 10 µl of solutions of N-hydroxysulfosuccinimide (sulfo-NHS from Pierce, Rockford US) and 10 µl 1-ethyl-3(3-dimethylaminopropyl)-carbodiimidhydrochlorid (EDC from Pierce), both diluted in activation buffer to 50 mg/ml, are added to stabilize the reaction and activate the beads. After mixing, the beads are incubated for 20 min, rotating in the dark at room temperature. The activated beads are subsequently washed with coupling buffer (mmol/l 2(N-morpholino ethanesulfonic acid, MES), pH 5.0), added 500 µl azide-free solution of capture antibody (100 µg/ml) and incubated rotating for 2 hours or overnight. Azide is removed from antibodies by dialysis (Slide-A-Lyzer® dialysis cassette, MWCO=10 000 from Pierce) in 3l PBS overnight at 4° C. After incubation, the beads are washed with washing buffer (PBS containing 0.05% Tween 20) and re-suspend in 75 µl blocking/storage buffer (PBS containing 1% Bovine serum albumin (BSA) and 0.05% sodium azide).

The beads are counted with a hemocytometer, adjusted to a concentration of $20 \times 10^6$ beads/ml with blocking/storage buffer and stored protected from light at 2-8° C.

The assay procedure is performed as follows: A filter plate (MultiScreen MABVN 1.2 µm 96-well, Millipore, Burlington US) are prepared by pre-wetting it with assay buffer (PBS containing 0.5% Tween 20 and 1% BSA). To each well are added 50 µl of sample pipetted from the microtiter wells after extraction (1000 divided in duplicates or 150 µl divided in triplicates) and a 50 µl suspension of capture-antibody-conjugated beads, 1500 beads per analyte in assay buffer containing 1% guinea pig/pig serum (1:1). The capture-antibodies react with their corresponding antigens during 1½ hour of incubation and unbound material is removed from the beads by filtering it through the wells using a MultiScreen Vacuum Manifold (Millipore). The beads are washed twice using 200 µl washing buffer (PBS containing 0.5% Tween) per well. The now captured antigens are reacted for 1½ hour with a mixture (50 µl) of biotinylated detection antibodies each diluted 1:1000 in assay buffer. 50 µl of streptavidin-phycoerythrin 20 µg/ml in assay buffer (Molecular Probes, The Netherlands) are added to the wells and the incubation continues for additional 30 min. The beads are finally washed twice with 200 µl washing buffer and re-suspended in 125 µl washing buffer. After 15 min of shaking, the samples are analyzed on the LUMINEX® 100™ system according to manufacturer's instructions.

In one embodiment, the samples are analyzed for content of cytokines, chemokines and growth factors (e.g. interleukins such as Il-1, Il-2, Il-3, Il-4, Il-5, Il-6, Il-7, Il-8, Il-9, Il-10, Il-11, Il-12, Il-13, Il-14, Il-15, Il-16, Il-17, Il-18, Il-19, Il-20, Il-21, Il-22, Il-23, Il-24, Il-25, Il-26, an interferon (IFN), a tumor necrosis factor (TNF), membrane cofactor protein (MCP), macrophage inflammatory protein (MIP), matrix metalloproteinase 9 (MMP-9), triggering receptor expressed on myeloid cells (TREM), macrophage (M)-colony stimulating factor (CSF) M-CSF, granulocyte (G)-CSF, granulocyte macrophage (GM)-CSF, chemokines such as CC (CC motif), CXC (C—X—C motif), growth factors such as transforming growth factor (TGF) TGFa, TGFβ, epidermal growth factor (EGF), vascular endothelial growth factor (VEGF), insulin-like growth factor IGF I, IGF II, insulin, inflammatory mediators such as histamine, prostaglandins, leukotrienes, thromboxanes) and/or neurotransmitters (e.g., serotonin, neurotrophin-4 and is brain derived neurotrophic factor).

In another embodiment the samples are analyzed for standard and specific clinical parameters such as CRP, IgG, IgA, IgM, IgD, IgE, specific (i.e. antigen specific) antibodies, transferrin, albumin, transthyretin, etc.

In another embodiment the biological fluid to be analyzed is a cerebrospinal fluid, a peritoneal fluid, a cyst fluid, an amniotic fluid, a lavage fluid, a saliva, a cell extract or a tissue extract.

In still another embodiment the source of cells are cell lines or isolated blood cells, manipulated cells, transgenic cells, transfected cells, or any cell type or altered or manipulated cell type.

The invention may be applied to blood and other body fluids and tissue extracts from any species and type of animal (e.g. human, monkey, mouse, rat, cow, dog, horse, cat, bird, fish and any other species) including transgenic animals.

In a special embodiment the test compound is immobilised on a solid surface (e.g. filter paper) and then incubated with a blood sample or a biological fluid or extract. After incubation, the filter paper is allowed to dry or the blood is spotted on filter paper and dried.

In a particular use of the invention, the volume of blood, biological fluid or extract is adjusted to allow interaction with an immobilised compound or a compound in solution for a fixed time while at the same time drying on the filter paper.

In one embodiment of the invention, a live test person or patient is infused with a test compound and blood samples are drawn from the person at certain time intervals, spotted on filter paper, dried and subsequently analyzed.

The blood samples may be drawn from test individuals using standard needles and equipment and carried out by trained personal. However, the drawing of blood may also be carried out using devices allowing local individual sampling.

In one embodiment, kits are provided. In a further embodiment, a kit includes, in a single or separate (multiple) containers, a test compound and filter papers. The kit may also include a container for mixing the test compound with a biological fluid sample. In another embodiment, the kit includes a container including a buffer solution for a control sample. Buffers are described above and may be selected by one of skill in the art. In a further embodiment, the kit includes a container for storage of the filter paper following application of a biological fluid sample and test compound. The kit may also include a container for storage of filter paper following application of a control sample. In still another embodiment, the kit includes a desiccant.

Desiccants include compounds which absorb water and compounds which reversibly bond with water, including anhydrous salts which absorb water or moisture and form a stable hydrated salt. In one embodiment, useful desiccants include magnesium chloride, calcium chloride and mixtures thereof. Other suitable desiccants include capillary desiccants which rely on fine capillaries between adjacent desiccant particles to absorb moisture.

The kits described herein may include any of the test compounds described above. In one embodiment, the test compound is an amino acid, a peptide, a protein, a carbohydrate, an oligosaccharide, a polysaccharide, a glycoprotein, a lipid, a lipoprotein, a glycosaminoglycan, a hormone, a steroid, a vitamin, and a low molecular weight synthetic compound which influences the blood to cause an alteration of its composition. In another embodiment, the test compound is a toxin, allergen, autoantigen, bacterial protein or polysaccharide, viral protein, fungal protein or polysaccharide, parasitic protein or polysaccharide, bacterial lipopolysaccharide or any other compound relevant to diseases.

The following examples are illustrative only and do not limit the scope of the invention.

EXAMPLES

Example 1

Drawing, Incubation, Spotting, Drying and Storage of Blood

From a test person (subject), 10 ml blood is drawn into an anticoagulant test tube using a sterile needle and syringe. The blood is divided in aliquots of 1 ml using sterile anticoagulant test tubes. From one sample, a blood sample is spotted directly on paper until the marked circle is full (the volume used is approximately 0.2 ml). To the other test tubes samples to be tested are added in predetermined concentrations and the test tubes are allowed to incubate at 37° C. or at ambient temperature for 1 h. Samples of 0.2 ml are then spotted from each on filter paper. The blood samples are spotted on filter paper with a capillary tube, pipette or similar in one layer and dried at room temperature, e.g., in a well ventilated hood or in an ambient place. Samples are then stored at −20° C. or room temperature under low humidity, so that the paper is kept dry. For this purpose, ordinary freezers may be used and the papers may be kept in envelopes or in desiccators.

Example 2

Extraction of Filter Paper and Analysis

Two filter paper disks, 3.2 mm in diameter, are punched out from DBSS or standards on filter paper and placed together in microtiter wells. 140 µl or 180 µl (for double- or triple-measurements, respectively) extraction buffer, PBS containing "Complete protease inhibitor cocktail with ethylenediamine tetra-acetic acid (EDTA)" (Roche, Germany) 1 tablet dissolved per 25 ml assay buffer (PBS containing 0.5% Tween 20 and 1% BSA), are added to each well and the analytes are extracted protected from light at room temperature on a plate shaker set at 600 rpm for 60 minutes.

Example 3

LUMINEX® Assay

Coupling of Antibodies to Beads:
Coupling of capture antibodies to carboxylated beads (Luminex corp., Austin Tex., US) are performed according to the manufacturer's instruction: $2.5 \times 10^6$ beads are washed twice with activation buffer (0.1 mol/l sodium phosphate, pH 6.2), re-suspended in 80 µl activation buffer and sonicated until a homogenous distribution of the beads are observed. 10 µl of solutions of N-hydroxysulfosuccinimide (sulfo-NHS from Pierce, Rockford US) and 10 µl 1-ethyl-3(3-dimethylaminopropyl)-carbodiimidhydrochloride (EDC from Pierce), both diluted in activation buffer to 50 mg/ml, are added to stabilize the reaction and activate the beads. After mixing, the beads are incubated for 20 min rotating in the dark at room temperature. The activated beads are subsequently washed with coupling buffer (mmol/l 2(N-morpholino ethanesulfonic acid, MES), pH 5.0), added 500 µl azide-free solution of capture antibody (100 µg/ml) and incubated rotating for 2 hours or overnight. Azide is removed from antibodies by dialysis (Slide-A-Lyzer® dialysis cassette, MWCO=10 000 from Pierce) in 3 l PBS overnight at 4° C. After incubation, the beads are washed with washing buffer (PBS containing 0.05% Tween 20) and re-suspended in 75 µl blocking/storage buffer (PBS containing 1% Bovine serum albumin (BSA) and 0.05% sodium azide).

The beads are counted with a hemocytometer, adjusted to a concentration of $20 \times 10^6$ beads/ml with blocking/storage buffer and stored protected from light at 2-8° C.

Example 4

Assay Procedure

A filter plate (MultiScreen MABVN 1.2 µm 96-well, Millipore, Burlington US) are prepared by pre-wetting it with assay buffer (PBS containing 0.5% Tween 20 and 1% BSA). To each well are added 50 µl of sample pipetted from the microtiter wells after extraction (100 µl divided in duplicates or 150 µl divided in triplicates) and a 50 µl suspension of capture-antibody-conjugated beads, 1500 beads per analyte in assay buffer containing 1% guinea pig/pig serum (1:1). The capture-antibodies react with their corresponding antigens during 1½ hour of incubation and unbound material is removed from the beads by filtering it through the wells using a MultiScreen Vacuum Manifold (Millipore). The beads are washed twice using 200 µl washing buffer (PBS containing 0.5% Tween) per well. The now captured antigens are reacted for 1½ hour with a mixture (50 µl) of biotinylated detection antibodies each diluted 1:1000 in assay buffer. 50 µl of streptavidin-phycoerythrin 20 µg/ml in assay buffer (Molecular Probes, The Netherlands) are added to the wells and the incubation continues for additional 30 min. The beads are finally washed twice with 200 µl washing buffer and re-suspended in 125 µl washing buffer. After 15 min of shaking, the samples are analyzed on the LUMINEX® 100™ system according to manufacturer's instructions.

Example 5

Test of Gc Globulin, Diphtheria Toxoid, Tetanus Toxoid and Lipopolysaccharide (LPS) for Cytokine Release The following solutions are mixed with blood from different persons and incubated at 37° C.:
1) 1 ml EDTA-blood (person X)+30 µl Gc batch 11
2) 1 ml EDTA-blood (person X)+30 µl Gc batch 13
3) 1 ml EDTA-blood (person Y)+30 µl Gc batch 11
4) 1 ml EDTA-blood (person Y)+30 µl Gc batch 13
5) 1 ml EDTA-blood (person X)+30 µl PBS
6) 1 ml EDTA-blood (person Y)+30 µl PBS
7) 1 ml EDTA-blood (person X)+30 µl Gc batch 11+50 µl LPS from *Klebsiella pneumoniae* (5 mg/ml)
8) 1 ml EDTA-blood (person X)+50 µl LPS from *Klebsiella pneumoniae* (5 mg/ml)
9) 1 ml EDTA-blood (person Z)+30 µl diphtheria toxoid (5.78 mg/ml)
10) 1 ml EDTA-blood (person Z)+30 µl tetanus toxoid (993 Lf/ml)
11) 1 ml EDTA-blood (person Z)+30 µl LPS from *Klebsiella pneumoniae* (5 mg/ml)
12) 1 ml EDTA-blood (person Z)+30 µl LPS from *Salmonella typhimurium* (5 mg/ml)
13) 1 ml EDTA-blood (person Z)+30 µl milliQ water After 1 min (A), 2 h (B), 24 h (C) and 48 h (D) 180 µl of each of the 8 solutions are spotted on filter paper and allowed to dry. Samples are subsequently (after 14 days storage at −20° C.) analyzed for content of cytokines using LUMINEX® technology (Skogstrand K, et al., Simultaneous measurement of 25 inflammatory markers and neurotrophins in neonatal dried blood spots by immunoassay with xMAP technology. *Clin Chem.* 2005; 51:1854-66). The results are shown in Table 1. It can be seen from the table that LPS induces large increases in IL-1b, IL-6, IL-8, MIP-1a, MIP-1β, while smaller but statistically significant changes are seen for other analytes. Diphteria toxoid induces an increase in MIP-1β.

TABLE 1

Test of Gc globulin, diphtheria toxoid, tetanus toxoid and lipopolysaccharide (LPS) for cytokine release (see Example 5 for details). All results are in pg/ml unless otherwise stated.

| Analyte | IL-1β | IL-2 | IL-4 | IL-5 | IL-6 | IL-8 | IL-10 | IL-12 | IL-17 | IL-18 | sIL-6ra ng/ml | IFN-γ | TNF-a | TNF-β | MCP-1 | TGF-β |
|---|---|---|---|---|---|---|---|---|---|---|---|---|---|---|---|---|
| 1A | 120 | 33 | 18 | 57 | 62 | 155 | 297 | 104 | 188 | 3674 | 1269.4 | 137 | 137 | 470 | 1795 | 828 |
| 1B | 71 | 26 | 14 | 55 | 52 | 148 | 289 | 91 | 138 | 2985 | 970.3 | 96 | 105 | 427 | 1462 | 594 |
| 1C | 111 | 31 | 24 | 48 | 35 | 7592 | 289 | 89 | 191 | 2357 | 695.2 | 36 | 85 | 519 | 1339 | 616 |
| 1D | 101 | 17 | 20 | 60 | 42 | 5680 | 279 | 89 | 156 | 1444 | 620.4 | 75 | 88 | 355 | 1296 | 1007 |
| 2A | 10 | 30 | 11 | 47 | 35 | 124 | 232 | 71 | 140 | 2818 | 900.9 | 39 | 69 | 503 | 1442 | 560 |
| 2B | 47 | 21 | 18 | 49 | 44 | 210 | 232 | 80 | 163 | 2637 | 902.8 | 60 | 78 | 427 | 1296 | 700 |
| 2C | 73 | 25 | 22 | 61 | 46 | 8471 | 258 | 93 | 161 | 2802 | 874.9 | 119 | 90 | 503 | 1391 | 937 |
| 2D | 104 | 34 | 21 | 45 | 35 | 7588 | 262 | 78 | 115 | 1758 | 799/5 | 84 | 76 | 412 | 800 | 789 |
| 3A | <3 | 9 | 6 | 20 | 4 | 25 | 45 | 12 | 101 | 1502 | 516.9 | 24 | 17 | 213 | 889 | 91 |
| 3B | 45 | 12 | 8 | 35 | 36 | 50 | 258 | 73 | 147 | 1600 | 498.1 | 28 | 70 | 434 | 903 | 430 |
| 3C | 38 | 17 | 7 | 30 | 18 | 1956 | 80 | 25 | 101 | 1050 | 395.5 | 11 | 48 | 293 | 597 | 282 |
| 3D | 55 | 15 | 6 | 40 | 43 | 2882 | 129 | 53 | 135 | 732 | 402.8 | 39 | 72 | 149 | 737 | 458 |
| 4A | 69 | 24 | 7 | 44 | 38 | 77 | 272 | 102 | 138 | 2308 | 769.9 | 107 | 115 | 358 | 1472 | 557 |
| 4B | 38 | 16 | 13 | 39 | 29 | 69 | 120 | 17 | 117 | 2003 | 613.8 | 28 | 56 | 332 | 1569 | 255 |
| 4C | 43 | 25 | 18 | 36 | 47 | 2456 | 117 | 64 | 182 | 1317 | 537.8 | 30 | 102 | 351 | 903 | 477 |
| 4D | 8 | 7 | 16 | 37 | 17 | 3346 | 43 | 39 | 94 | 727 | 430.0 | 15 | 70 | 165 | 597 | 414 |
| 5A | 32 | 21 | 16 | 19 | 20 | 84 | 80 | 60 | 133 | 2535 | 876.4 | 39 | 95 | 427 | 1616 | 490 |
| 5B | 25 | 22 | 11 | 29 | 18 | 110 | 67 | 25 | 122 | 2581 | 870.3 | 46 | 65 | 383 | 1391 | 446 |
| 5C | 1 | 4 | 12 | 26 | <3 | 3695 | 23 | <3 | 70 | 1874 | 636.0 | <3 | 26 | 261 | 889 | 273 |
| 5D | 69 | 19 | 21 | 43 | 16 | 6488 | 166 | 44 | 122 | 1543 | 735.2 | 25 | 74 | 204 | 1540 | 870 |
| 6A | 20 | 15 | 7 | 25 | 22 | 94 | 155 | 69 | 133 | 1980 | 651.5 | 74 | 105 | 284 | 1401 | 479 |
| 6B | 45 | 24 | 16 | 37 | 44 | 68 | 82 | 80 | 152 | 1980 | 600.3 | 60 | 86 | 289 | 1124 | 506 |
| 6C | 30 | 8 | 8 | 36 | 20 | 3055 | 61 | 2 | 67 | 1058 | 411.7 | 29 | 48 | 104 | 889 | 417 |

TABLE 1-continued

Test of Gc globulin, diphtheria toxoid, tetanus toxoid and lipopolysaccharide (LPS)
for cytokine release (see Example 5 for details). All results are in pg/ml unless otherwise stated.

| | | | | | | | | | | | | | | | | |
|---|---|---|---|---|---|---|---|---|---|---|---|---|---|---|---|---|
| 6D | <3 | <3 | <3 | <3 | <3 | 1781 | <3 | <3 | <3 | 155 | 138.1 | <3 | <3 | <6 | <6 | <50 |
| 7A | <3 | 24 | 15 | 24 | 26 | 81 | 115 | 27 | 124 | 2213 | 802.3 | 11 | 38 | 332 | 1472 | 183 |
| 7B | 1223 | 25 | 24 | 28 | 578 | 2982 | 84 | 78 | 165 | 2234 | 712.3 | 14 | 724 | 371 | 1172 | 446 |
| 7C | 14429 | 20 | 23 | 36 | 14077 | 13606 | 204 | 115 | 244 | 2686 | 706.2 | 964 | 1399 | 418 | 1422 | 529 |
| 7D | 9413 | 15 | 15 | 39 | 11048 | 15148 | 117 | 108 | 228 | 1567 | 540.9 | 468 | 1020 | 342 | 860 | 594 |
| 8A | 901 | 23 | 15 | 28 | 40 | 237 | 103 | 29 | 152 | 2627 | 915/1 | 41 | 52 | 341 | 1597 | 450 |
| 8B | 1584 | 19 | 19 | 40 | 789 | 3494 | 101 | 66 | 251 | 2380 | 820/7 | 80 | 997 | 518 | 1328 | 344 |
| 8C | 11466 | 18 | 26 | 33 | 12878 | 13903 | 345 | 119 | 320 | 1809 | 620.1 | 339 | 1512 | 468 | 1391 | 705 |
| 8D | 7402 | 16 | 12 | 23 | 11902 | 14428 | 222 | 95 | 219 | 878 | 562.9 | 190 | 1471 | 268 | 753 | 438 |
| 9B | 148 | 33 | 20 | 20 | 21 | 1785 | 46 | 12 | 88 | 1058 | 833.4 | <3 | 81 | 350 | 875 | 624 |
| 9C | 138 | 28 | 23 | 31 | 17 | 10091 | 3 | 12 | 149 | 1272 | 724.8 | 1 | 95 | 316 | 652 | 894 |
| 10B | 25 | 37 | 22 | 15 | 14 | 383 | 92 | 7 | 106 | 1042 | 820.7 | 4 | 44 | 303 | 931 | 357 |
| 10C | 69 | 28 | 22 | 23 | 11 | 9921 | 39 | <3 | 110 | 987 | 664.7 | 6 | 61 | 268 | 56 | 578 |
| 11B | 2948 | 24 | 43 | 21 | 1697 | 58145 | 103 | 78 | 183 | 1456 | 442.1 | 68 | 1205 | 222 | 489 | 623 |
| 11C | 16953 | 37 | 24 | 66 | 4215 | 757774 | 299 | 73 | 264 | 1070 | 374.1 | 73 | 983 | 274 | 91 | 528 |
| 12B | 1665 | 26 | 19 | 46 | 1539 | 16428 | 25 | 28 | 148 | 1153 | 382.8 | 129 | 844 | 388 | 247 | 479 |
| 12C | 12805 | 32 | 21 | 39 | 3715 | 541309 | 100 | 70 | 268 | 1450 | 339.3 | 80 | 750 | 274 | 680 | 907 |
| 13B | 83 | 17 | 14 | 37 | <3 | 252 | 7 | 51 | 70 | 1017 | 351.4 | 27 | 19 | 328 | 389 | 554 |
| 13C | 60 | 29 | 17 | 21 | <3 | 67105 | 2 | 44 | 74 | 1384 | 361.4 | 225 | 40 | 326 | 273 | 508 |

| Analyte | MIP-1a | MIP-1β | MMP-9 µg/ml | TREM-1 | BDNF ng/ml | GM-CSF | NT-4 | CRP µg/ml | RANTES ng/ml | int. st. dev. % |
|---|---|---|---|---|---|---|---|---|---|---|
| 1A | 286 | 1313 | 1.40 | 3509 | 16.2 | 63 | 85 | 0.68 | 188.0 | 32 |
| 1B | 174 | 1285 | 1.19 | 3917 | 11.2 | 52 | 84 | 0.53 | 136.8 | 10 |
| 1C | 221 | 1091 | 1.36 | 2609 | 14.2 | 62 | 43 | 0.43 | 158.3 | −7 |
| 1D | 210 | 549 | 1/05 | 2848 | 14.2 | 112 | 105 | 0.40 | 118.8 | 21 |
| 2A | 254 | 1387 | 1.20 | 2848 | 11.9 | 65 | 90 | 0.49 | 153.0 | −4 |
| 2B | 192 | 1305 | 1/12 | 3001 | 11.6 | 88 | 57 | 0.53 | 116.7 | 7 |
| 2C | 200 | 1055 | 1.33 | 2925 | 17.7 | 88 | 72 | 0.52 | 191.1 | 20 |
| 2D | 219 | 677 | 1.16 | 3223 | 19.1 | 170 | 110 | 0.44 | 160.8 | 12 |
| 3A | 73 | 852 | 1.15 | 2609 | 6.2 | 25 | 35 | 0.38 | 55.6 | −8 |
| 3B | 106 | 1067 | 1.15 | 2443 | 6.9 | 86 | 52 | 0.57 | 50.2 | 15 |
| 3C | 154 | 627 | 1.26 | 2181 | 8.9 | 45 | 40 | 0.36 | 57.9 | −5 |
| 3D | 137 | 193 | 1.13 | 2690 | 8.9 | 82 | 47 | 0.38 | 51.7 | 13 |
| 4A | 192 | 1124 | 1.59 | 3983 | 10.8 | 51 | 100 | 0.93 | 97.3 | 37 |
| 4B | 112 | 996 | 1.51 | 2609 | 9.7 | 60 | 60 | 0.48 | 92.1 | 9 |
| 4C | 201 | 716 | 1.37 | 2925 | 11.0 | 83 | 70 | 0.51 | 88.8 | 6 |
| 4D | 96 | 199 | 1.32 | 1696 | 11.0 | 85 | 53 | 0.37 | 82.7 | 1 |
| 5A | 192 | 1327 | 1/11 | 1358 | 11.0 | 41 | 43 | 0.48 | 127.2 | −4 |
| 5B | 167 | 1196 | 1/02 | 1800 | 10.9 | 22 | 57 | 0.44 | 119.8 | −7 |
| 5C | 88 | 940 | 1/03 | 2690 | 11.8 | 15 | 47 | 0.30 | 115.6 | −6 |
| 5D | 219 | 702 | 1/30 | 3001 | 17.4 | 76 | 85 | 0.37 | 176.5 | 3 |
| 6A | 187 | 919 | 1/37 | 3223 | 9.5 | 68 | 74 | 0.63 | 84.2 | 18 |
| 6B | 214 | 1087 | 1/31 | 3438 | 8.3 | 59 | 82 | 0.58 | 70.6 | 15 |
| 6C | 118 | 495 | 1.19 | 2090 | 8.0 | <6 | 42 | 0.36 | 59.9 | 4 |
| 6D | <6 | <6 | 0.72 | <313 | 2.9 | <6 | <3 | 0.03 | 20.3 | −53 |
| 7A | 51 | 1097 | 0.97 | 1231 | 9.2 | 48 | 45 | 0.38 | 118.4 | −41 |
| 7B | 4706 | 21819 | 1.05 | <313 | 10.4 | 100 | 55 | 0.34 | 129.4 | −1 |
| 7C | 15802 | 32037 | 1.05 | 3076 | 15.6 | 76 | 67 | 0.34 | 159.3 | −1 |
| 7D | 15112 | 29767 | 0.74 | 2443 | 12.6 | 114 | 74 | 0.31 | 116.9 | −4 |
| 8A | 257 | 1349 | 1.09 | 3438 | 11.2 | 70 | 77 | 0.42 | 130.7 | −3 |
| 8B | 5333 | 24582 | 1/13 | 3368 | 11.8 | 91 | 105 | 0.42 | 112.4 | 10 |
| 8C | 14303 | 31580 | 1./04 | 3296 | 10.9 | 100 | 63 | 0.36 | 144.6 | 2 |
| 8D | 14937 | 28500 | 0.89 | 1476 | 13.4 | 106 | 30 | 0.28 | 106.3 | −3 |
| 9B | 591 | 6076 | 1.42 | 1996 | 22.8 | 59 | 35 | 0.60 | 161.3 | −1 |
| 9C | 643 | 5472 | 1.28 | 1476 | 26.2 | 83 | 55 | 0.55 | 141.6 | −9 |
| 10B | 96 | 1099 | 1.43 | 2090 | 20.0 | 82 | 53 | 0.60 | 154.9 | −8 |
| 10C | 141 | 950 | 1.26 | 1899 | 23.7 | 59 | 55 | 0.50 | 137.7 | −6 |
| 11B | 5992 | 22797 | 2.10 | 2920 | 30.1 | 14 | 51 | 1.08 | 240.6 | 10 |
| 11C | 11035 | 26838 | 1.51 | 2087 | 32.8 | 15 | 63 | 0.83 | 183.0 | 2 |
| 12B | 4055 | 19656 | 1.81 | 2920 | 18.8 | 10 | 24 | 0.92 | 163.0 | 5 |
| 12C | 8644 | 26995 | 1.45 | 3257 | 26.2 | 23 | 15 | 0.76 | 175.0 | −9 |
| 13B | 142 | 1351 | 1.50 | 2747 | 16.7 | 12 | 35 | 0.86 | 159.8 | −10 |
| 13C | 77 | 1087 | 1.67 | 2920 | 22.9 | 2 | 13 | 0.76 | 164.7 | −2 |

NT-4 is neurotrophin-4;
BDNF is brain derivated neurotrophic factor.

Example 6

Test of Diphtheria Toxoid, Tetanus Toxoid, Tuberculin PPD and BCG for Cytokine Release The following 6 solutions are mixed and incubated at 37° C.:
1) 1 ml EDTA-blood (person Y)+30 μl diphtheria toxoid (5.78 mg/ml)
2) 1 ml EDTA-blood (person Y)+30 μl tetanus toxoid (993 Lf/ml)
3) 1 ml EDTA-blood (person Y)+30 μl BCG (4-16×10$^6$ cfU/ml)
4) 1 ml EDTA-blood (person Y)+30 μl tuberculin PPD (0.4 μg/ml)
5) 1 ml EDTA-blood (person Y)+30 μl milliQ water
6) 1 ml EDTA-blood (person Y)+30 μl BCG vaccine solvent (control)

After 1 min (A), 2 h (B), 4 h (C) 6 h (D), and 24 h (E) 180 μl of each of the 6 solutions are spotted on filter paper and allowed to dry. Samples are subsequently (after storage at −20° C. for 30 days) analyzed for content of cytokines using LUMINEX® technology (22). The results are shown in Table 2. From the table it can be seen that BCG induces a large increase in IL-8 and MIP-1b compared with the control. Similarly, diphtheria toxoid, tetanus toxoid and PPD induces increases in IL-8 and MIP-1β, while smaller but statistically significant changes are seen for other analytes.

TABLE 2

Test of diphtheria toxoid, tetanus toxoid, tuberculin PPD and BCG for cytokine release (see example 6 for details). All results are in pg/ml unless otherwise stated.

| analyte | IL-1b | IL-2 | IL-4 | IL-5 | IL-6 | IL-8 | IL-10 | IL-12 | IL-17 | IL-18 |
|---|---|---|---|---|---|---|---|---|---|---|
| 1A | 47 | 42 | 9 | 11 | 161 | 99 | 477 | 160 | 73 | 2609 |
| 1B | 54 | 76 | 11 | 14 | 130 | 284 | 394 | 201 | 69 | 3761 |
| 1C | 90 | 146 | 27 | 8 | 115 | 588 | 637 | 226 | 87 | 2564 |
| 1D | 97 | 124 | 26 | 22 | 217 | 783 | 706 | 267 | 111 | 3282 |
| 1E | 106 | 153 | 17 | 20 | 135 | 7290 | 981 | 336 | 83 | 1745 |
| 2A | 29 | 8 | 4 | 11 | 73 | 95 | 61 | 132 | 43 | 2233 |
| 2B | 44 | 77 | 13 | 7 | 93 | 135 | 410 | 217 | 47 | 2202 |
| 2C | 43 | 82 | 14 | 10 | 103 | 187 | 493 | 233 | 68 | 2726 |
| 2D | 57 | 113 | 16 | 12 | 110 | 234 | 468 | 139 | 86 | 3265 |
| 2E | 54 | 120 | 8 | 10 | 143 | 6335 | 811 | 185 | 63 | 1707 |
| 3A | 33 | 26 | 26 | 33 | 75 | 113 | 240 | 213 | 78 | 2934 |
| 3B | 77 | 93 | 14 | 2 | 97 | 268 | 268 | 158 | 56 | 2556 |
| 3C | 160 | 155 | 11 | 18 | 127 | 998 | 533 | 252 | 54 | 2763 |
| 3D | 145 | <3 | 24 | 13 | 49 | 1439 | 378 | 76 | 54 | 3104 |
| 3E | 113 | 92 | 3 | 10 | 67 | 27779 | 202 | 120 | 75 | 1597 |
| 4A | 152 | 96 | 2 | 4 | 125 | 149 | 323 | 183 | 47 | 2461 |
| 4B | 43 | 268 | 16 | 20 | 64 | 160 | 286 | 137 | 53 | 2512 |
| 4C | 31 | 79 | 14 | 20 | 60 | 189 | 376 | 140 | 77 | 2567 |
| 4D | 665 | 71 | 568 | 687 | 493 | 465 | 1812 | 746 | 1355 | 3170 |
| 4E | 70 | <3 | 8 | 13 | 81 | 7011 | 386 | 202 | 59 | 2432 |
| 5A | 48 | 68 | 14 | 9 | 26 | 136 | 259 | 77 | 34 | 2660 |
| 5B | 44 | 220 | 14 | 3 | 46 | 117 | 168 | 109 | 38 | 2461 |
| 5C | 23 | 195 | 2 | 8 | 63 | 114 | 444 | 76 | 64 | 2221 |
| 5D | 25 | 179 | 9 | 11 | 100 | 174 | 350 | 133 | 60 | 2982 |
| 5E | 30 | 218 | 13 | 8 | 25 | 3558 | 417 | 146 | 79 | 1478 |
| 6A | 27 | 121 | 16 | 10 | 46 | 126 | 461 | 154 | 51 | 2406 |
| 6B | 32 | 95 | 10 | 3 | 34 | 128 | 400 | 149 | 41 | 2353 |
| 6C | 19 | 101 | 13 | 24 | 9 | 131 | 256 | 91 | 71 | 2413 |
| 6D | 50 | 102 | 7 | 22 | 70 | 163 | 281 | 183 | 51 | 2876 |
| 6E | 27 | 97 | 10 | 11 | 87 | 5038 | 404 | 155 | 69 | 1474 |

| analyte | sIL-6ra ng/ml | IFN-γ | TNF-a | TNF-β | MCP-1 | TGF-β |
|---|---|---|---|---|---|---|
| 1A | 1016.9 | 78 | 61 | 1392 | 2869 | 816 |
| 1B | 1218.9 | 118 | 39 | 1474 | 2288 | 210 |
| 1C | 822.0 | 209 | 109 | 1569 | 2126 | 556 |
| 1D | 1091.7 | 165 | 150 | 1872 | 3048 | 791 |
| 1E | 863.0 | 155 | 136 | 1724 | 2213 | 852 |
| 2A | 857.1 | 72 | 158 | 1329 | 1600 | 276 |
| 2B | 839.0 | 57 | 7 | 1865 | 1760 | 554 |
| 2C | 955.2 | 52 | 90 | 1390 | 1794 | 515 |
| 2D | 1095.0 | 109 | 77 | 1599 | 2838 | 582 |
| 2E | 835.5 | 91 | 34 | 1308 | 1990 | 551 |
| 3A | 981.4 | <3 | 69 | 1187 | 1506 | 671 |
| 3B | 851.1 | 59 | 60 | 1291 | 2041 | 471 |
| 3C | 985.7 | 153 | 59 | 1454 | 2543 | 405 |
| 3D | 1045.6 | 67 | 48 | 1351 | 1500 | 542 |
| 3E | 787.5 | 9 | 112 | 1183 | 1240 | 508 |
| 4A | 941.4 | 71 | 60 | 1807 | 2800 | 623 |
| 4B | 833.1 | 107 | 72 | 1310 | 1766 | 527 |
| 4C | 937.6 | 165 | 112 | 1563 | 1211 | 384 |
| 4D | 1186.3 | 93 | 247 | 2142 | 6253 | 113 |
| 4E | 966.0 | 6 | 59 | 1012 | 1234 | 579 |
| 5A | 885.7 | 5 | 35 | 1283 | 1473 | 305 |
| 5B | 887.3 | 62 | 21 | 1593 | 2341 | 284 |
| 5C | 735.4 | 229 | 65 | 1522 | 1262 | 520 |

TABLE 2-continued

Test of diphtheria toxoid, tetanus toxoid, tuberculin PPD and BCG for cytokine release (see example 6 for details). All results are in pg/ml unless otherwise stated.

| | | | | | | |
|---|---|---|---|---|---|---|
| 5D | 1042.6 | 154 | 129 | 1535 | 2441 | 426 |
| 5E | 802.9 | 172 | 69 | 1602 | 107 | 256 |
| 6A | 852.2 | 122 | 45 | 1674 | 1996 | 627 |
| 6B | 758.5 | 41 | 97 | 1664 | 1189 | 372 |
| 6C | 695.6 | 30 | 62 | 1492 | 884 | 378 |
| 6D | 943.3 | 177 | 16 | 1516 | 736 | 473 |
| 6E | 808.6 | 60 | 91 | 1305 | 1256 | 619 |

| analyte | MIP-1a | MIP-1β | MMP-9 µg/ml | TREM-1 | BDNF ng/ml | GM-CSF | NT-4 | CRP µg/ml | RANTES ng/ml | int, st, dev, % |
|---|---|---|---|---|---|---|---|---|---|---|
| 1A | 85 | 1307 | 11.3 | 5676 | 8.0 | 21 | 23 | 0.46 | 56.2 | 6 |
| 1B | 182 | 2534 | 15.6 | 6485 | 12.2 | 22 | 24 | 0.55 | 62.8 | −1 |
| 1C | 210 | 2883 | 14.1 | 6254 | 10.9 | 22 | 17 | 0.49 | 59.0 | 5 |
| 1D | 224 | 3102 | 17.2 | 6562 | 13.0 | 26 | 33 | 0.57 | 71.8 | 9 |
| 1E | 205 | 1053 | 14.3 | 5792 | 10.6 | 45 | 41 | 0.48 | 65.3 | 0 |
| 2A | 75 | 1308 | 7.4 | 4821 | 7.1 | 19 | 16 | 0.38 | 50.0 | −1 |
| 2B | 116 | 1345 | 13.1 | 5599 | 8.3 | 24 | 13 | 0.41 | 55.1 | 3 |
| 2C | 99 | 1163 | 17.7 | 5521 | 10.7 | 18 | 24 | 0.50 | 63.2 | 0 |
| 2D | 70 | 1234 | 19.1 | 5521 | 10.7 | 25 | 20 | 0.53 | 59.3 | 1 |
| 2E | 125 | 375 | 27.0 | 5985 | 11.4 | 41 | 23 | 0.45 | 56.9 | 0 |
| 3A | 112 | 1189 | 12.0 | 7747 | 8.3 | 17 | 28 | 0.48 | 45.3 | −4 |
| 3B | 235 | 3717 | 8.1 | 5289 | 9.0 | 20 | 14 | 0.39 | 41.8 | 4 |
| 3C | 410 | 7922 | 15.3 | 4860 | 9.2 | 20 | 26 | 0.45 | 41.5 | 2 |
| 3D | 296 | 8706 | 10.8 | 7289 | 11.0 | 23 | 20 | 0.44 | 47.3 | 1 |
| 3E | 281 | 6280 | 14.2 | 4232 | 12.3 | 33 | 17 | 0.38 | 42.5 | −12 |
| 4A | 128 | 1397 | 11.0 | 5715 | 9.1 | 20 | 20 | 0.47 | 39.6 | 4 |
| 4B | 110 | 1159 | 10.7 | 5483 | 8.5 | 17 | 24 | 0.46 | 46.3 | −1 |
| 4C | 45 | 1122 | 10.0 | 3356 | 9.5 | 18 | 22 | 0.45 | 46.0 | −4 |
| 4D | 866 | 1301 | 15.4 | 21919 | 12.4 | 36 | 447 | 0.44 | 43.3 | −5 |
| 4E | 64 | 183 | 19.6 | 5521 | 8.3 | 37 | 15 | 0.45 | 47.3 | −11 |
| 5A | 69 | 993 | 15.3 | 4938 | 9.4 | 19 | 16 | 0.46 | 44.6 | −5 |
| 5B | 4 | 1087 | 10.4 | 4743 | 8.9 | 19 | 15 | 0.39 | 43.2 | 2 |
| 5C | 60 | 1248 | 8.1 | 5521 | 8.3 | 23 | 15 | 0.45 | 45.6 | 2 |
| 5D | 41 | 1296 | 21.3 | 4035 | 12.5 | 28 | 20 | 0.52 | 50.5 | 3 |
| 5E | 35 | 388 | 8.7 | 4272 | 10.7 | 42 | 5 | 0.40 | 46.1 | −17 |
| 6A | 57 | 1200 | 11.8 | 6331 | 8.2 | 19 | 13 | 0.45 | 49.1 | 1 |
| 6B | 98 | 1117 | 13.5 | 7251 | 8.5 | 21 | 18 | 0.42 | 48.6 | 0 |
| 6C | 85 | 1228 | 10.1 | 5016 | 7.5 | 22 | 33 | 0.40 | 46.4 | −7 |
| 6D | 66 | 1118 | 20.6 | 6101 | 9.6 | 27 | 24 | 0.47 | 49.5 | 4 |
| 6E | 83 | 256 | 11.9 | 4469 | 10.7 | 39 | 14 | 0.39 | 50.8 | −9 |

Example 7

Storage of Samples for Extended Periods of Time

Dried blood spot samples (DBSS) should be stored dried and preferable at about −20° C. Room temperature can also be used as long as the samples are protected from moisture.

In Denmark all residual DBSS have since 1982 been stored in a biological specimen bank at −24° C., in accordance with regulations from the Ministry of Health (Norgaard-Pedersen B, Simonsen H. Biological specimen banks in neonatal screening. *Acta Paediatr Suppl* 1999; 88:106-9). For stability studies, DBSS stored for 23 years, 3 years and 1 month respectively, were taken anonymously from the Danish DBSS specimen bank. The mean concentrations of each analyte from each period were calculated from 10 samples and compared to routinely collected anonymous DBSS that were stored in the laboratory for 2 weeks at −20° C. (Table 3). It can be seen that within experimental error, there is no deterioration of the samples even upon 23 years of storage.

TABLE 3

Analysis of samples stored for short (1 month), long (3 years) and extended (23 years) periods of time. Results are expressed as per cent of concentration detectable in 2 week old DBSS not yet put to storage in the PKU-biobank. Samples were extracted and analyzed as described in Examples 2-4.

| | 23 years | 3 years | 1 month |
|---|---|---|---|
| IL-1β | 44 | 43 | 93 |
| IL-2 | 116 | 115 | 113 |
| IL-4 | 91 | 91 | 107 |
| IL-5 | 105 | 116 | 122 |
| IL-6 | 95 | 101 | 108 |
| IL-8 | 28 | 38 | 64 |
| IL-10 | 124 | 103 | 129 |
| IL-12 | 95 | 108 | 107 |
| IL-17 | 94 | 100 | 107 |
| IL-18 | 138 | 113 | 129 |
| TNF-a | 92 | 101 | 109 |
| TNF-β | 88 | 94 | 93 |
| IFN-γ | 117 | 119 | 121 |
| RANTES | 87 | 89 | 90 |
| MCP-1 | 94 | 112 | 112 |
| GM-CSF | 102 | 107 | 108 |
| MIP-1a | 85 | 88 | 98 |
| MIP-1β | 59 | 76 | 79 |
| sIL-6ra | 48 | 101 | 113 |
| TGF-β | 111 | 100 | 95 |
| MMP-9 | 57 | 49 | 93 |
| TREM-1 | 68 | 84 | 129 |

TABLE 3-continued

Analysis of samples stored for short (1 month), long (3 years) and extended (23 years) periods of time. Results are expressed as per cent of concentration detectable in 2 week old DBSS not yet put to storage in the PKU-biobank. Samples were extracted and analyzed as described in Examples 2-4.

|      | 23 years | 3 years | 1 month |
|------|----------|---------|---------|
| CRP  | 73       | 123     | 110     |
| BDNF | 22       | 54      | 58      |
| NT-4 | 54       | 63      | 111     |

All publications cited in this specification are incorporated herein by reference. While the invention has been described with reference to particularly preferred embodiments, it will be appreciated that these embodiments are not limitation upon the scope of the claims.

The invention claimed is:

1. A method for preparing a biological fluid sample for analysis, said method comprising:
   (a) initiating a reaction by mixing said biological fluid sample with a test compound, wherein said test compound interacts with constituents of said biological fluid sample to cause an alteration in the composition of said biological fluid sample;
   (b) stopping the reaction by spotting the biological fluid sample and test compound mixture on filter paper and drying the spotted mixture on said filter paper;
   wherein the test compound is selected from the group consisting of a toxin, allergen, autoantigen, bacterial protein or polysaccharide, viral protein, fungal protein or polysaccharide, parasitic protein or polysaccharide, and bacterial lipopolysaccharide.

2. The method according to claim 1, wherein the biological fluid sample is blood.

3. The method according to claim 1, wherein the biological fluid sample is a cerebrospinal fluid, a peritoneal fluid, a cyst fluid, an amniotic fluid, a lavage fluid, a saliva, a cell extract or a tissue extract.

4. A method for analysing the effect of a test compound on a biological fluid sample prepared for analysis by the method according claim 1, comprising analysing said biological fluid sample and test compound mixture on said filter paper for the content of cytokines, chemokines and growth factors and/or neurotransmitters or other polypeptides and proteins produced by said reaction.

5. A method for analysing the effect of a test compound on a biological fluid sample prepared for analysis by the method according claim 1, comprising analysing said biological fluid sample and test compound mixture on said filter paper for the content of clinical parameters such as CRP, IgG, IgA, IgM, IgD, IgE, antigen-specific antibodies, transferrin, albumin and/or transthyretin produced by said reaction.

6. A method for analysing the effect of a test compound on a biological fluid sample prepared for analysis by the method according to claim 1, comprising analysing said biological fluid sample and test compound mixture on said filter paper by immunoassay, bioassay, mass spectrometry, high performance liquid chromatography (HPLC), gas chromatography (GC), or gas chromatography mass spectrometry (GC-MS).

7. The method according to claim 6, comprising analysing said biological fluid sample and test compound mixture on said filter paper by enzyme-linked immunosorbent assay (ELISA), fluorescence-linked immunosorbent assay (FLISA), fluorescence assay, luminescence assay, electrochemiluminescence assay, scintillation proximity assay, radioimmunoassay, matrix-assisted laser desorption/ionization mass spectrometry (MALDI-MS), electrospray ionization mass spectrometry (ESI-MS), ambient mass spectrometry (ambient-MS), or desorption electrospray ionization mass spectrometry (DESI-MS).

* * * * *